United States Patent
Torrie (10) Patent No.: US 10,206,690 B2
(45) Date of Patent: Feb. 19, 2019

(54) BONE AND TISSUE MARKER

(75) Inventor: Paul Alexander Torrie, Marlborough, MA (US)

(73) Assignee: Smith & Nephew, Inc., Memphis, TN (US)

(*) Notice: Subject to any disclaimer, the term of this patent is extended or adjusted under 35 U.S.C. 154(b) by 566 days.

(21) Appl. No.: 13/173,713

(22) Filed: Jun. 30, 2011

(65) Prior Publication Data
US 2012/0004691 A1  Jan. 5, 2012

Related U.S. Application Data (60) Provisional application No. 61/359,852, filed on Jun. 30, 2010.

(51) Int. Cl.
*A61B 17/56* (2006.01)
*A61B 17/16* (2006.01)
*A61B 90/00* (2016.01)
*A61B 18/14* (2006.01)

(52) U.S. Cl.
CPC .......... *A61B 17/1604* (2013.01); *A61B 90/39* (2016.02); *A61B 17/1668* (2013.01); *A61B 17/1682* (2013.01); *A61B 18/1445* (2013.01); *A61B 2090/395* (2016.02); *A61B 2090/3916* (2016.02); *A61B 2090/3937* (2016.02)

(58) Field of Classification Search
CPC ...... A61B 2019/5437; A61B 2019/545; A61B 2019/5405; A61B 2019/5416; A61B 19/54; A61B 16/1668; A61B 16/1682; A61B 16/1604; A61B 18/14; A61B 18/1445; A61B 2018/1412; A61B 90/06; A61B 2090/061

USPC .......... 606/86 R, 79–80, 87–90, 102, 84–85; 623/908
See application file for complete search history.

(56) References Cited

U.S. PATENT DOCUMENTS

| | | | |
|---|---|---|---|
| 1,722,748 A | 7/1929 | Holden, Jr. | |
| 3,776,649 A | 12/1973 | Kemezys | |
| 4,528,980 A | 7/1985 | Kenna | |
| 5,269,785 A * | 12/1993 | Bonutti | 606/80 |
| 5,339,799 A * | 8/1994 | Kami et al. | 600/117 |

(Continued)

FOREIGN PATENT DOCUMENTS

| | | |
|---|---|---|
| DE | 29814889 U1 | 12/1999 |
| EP | 0337901 A1 | 10/1989 |

(Continued)

OTHER PUBLICATIONS

International Search Report and Written Opinion for International Patent Application PCT/US2011/042676 dated Oct. 28, 2011.

(Continued)

*Primary Examiner* — Eric S Gibson
*Assistant Examiner* — Marcela I Shirsat
(74) *Attorney, Agent, or Firm* — Burns & Levinson, LLP; Joseph M. Maraia (57) ABSTRACT

The present invention concerns a marker for bones, particularly for marking irregularities in the femoral head. There is described a surgical instrument having a shaft including a handle towards a proximal end and an arm towards a distal end. The arm includes a template, and the arm and/or template further includes tissue marking means for marking differences in the curvature of a tissue surface.

23 Claims, 7 Drawing Sheets

(56) References Cited

U.S. PATENT DOCUMENTS

| | | | |
|---|---|---|---|
| 5,785,707 A * | 7/1998 | Boyd | A61B 18/1402 606/41 |
| 6,022,362 A * | 2/2000 | Lee et al. | 606/159 |
| 6,146,395 A | 11/2000 | Kanz et al. | |
| 6,231,611 B1 * | 5/2001 | Mosseri | A61B 17/1666 623/22.12 |
| 6,375,684 B1 | 4/2002 | Kriek | |
| 6,622,731 B2 * | 9/2003 | Daniel et al. | 128/898 |
| 7,516,672 B2 | 4/2009 | Schroll | |
| 9,750,491 B2 * | 9/2017 | Boettner | A61B 17/0218 |
| 2002/0072745 A1 * | 6/2002 | Truckai | A61B 18/1482 606/47 |
| 2003/0130741 A1 | 7/2003 | McMinn | |
| 2005/0060039 A1 | 3/2005 | Cyprien | |
| 2005/0197661 A1 | 9/2005 | Carrison et al. | |
| 2006/0004369 A1 * | 1/2006 | Patel et al. | 606/79 |
| 2006/0079963 A1 | 4/2006 | Hansen | |
| 2006/0084368 A1 * | 4/2006 | Kapgan | B23B 51/101 451/51 |
| 2006/0100632 A1 * | 5/2006 | Fell | 606/81 |
| 2006/0111722 A1 | 5/2006 | Bouadi | |
| 2007/0118135 A1 * | 5/2007 | Mansmann | 606/80 |
| 2007/0260256 A1 * | 11/2007 | Beaule | A61B 17/1668 606/80 |
| 2007/0288029 A1 * | 12/2007 | Justin et al. | 606/87 |
| 2009/0012526 A1 | 1/2009 | Fletcher | |
| 2009/0281545 A1 | 11/2009 | Stubbs | |
| 2010/0049200 A1 * | 2/2010 | Re | 606/89 |
| 2011/0270256 A1 * | 11/2011 | Nelson et al. | 606/85 |
| 2012/0046526 A1 | 2/2012 | Boettner et al. | |

FOREIGN PATENT DOCUMENTS

| | | |
|---|---|---|
| EP | 1669034 A1 | 6/2006 |
| FR | 319 465 A | 11/1902 |
| FR | 2833478 A1 | 6/2003 |
| JP | H0661215 U | 8/1994 |
| WO | 2010033473 A3 | 3/2010 |

OTHER PUBLICATIONS

International Search Report and Written Opinion for PCT/US2011/042672 dated Nov. 8, 2011.

* cited by examiner

BONE AND TISSUE MARKER

The present invention concerns a marker for bones. In particular, the present invention relates to a bone marker for marking irregularities in the femoral head.

In many joints, and in particular the hip joint, when the bones forming the joint are operated at the extremes in their range of motion, interference can occur between the bones. In the hip, for example, when the femur is flexed upwards it may collide with the rim of the socket or acetabulum, of the pelvis. When this occurs, any soft tissue which is caught between the colliding bones may be damaged and cause pain. The soft tissue that is caught is usually the labium, which is a ring-like structure formed from cartilage that surrounds the acetabular rim.

The cartilage tissue is generally damaged as a result of the high sheer forces that the joint is subjected to through movement at the extreme limits in its mobility. This is particularly damaging to the patient because the cartilage acts as a buffer between adjacent bone surfaces of joints and provides the sliding surfaces which allow the joint to move fluidly. This helps to prevent wear and tear on the joint by stopping the bones of the joint from directly grinding against one another.

Cartilage tissue only has a very limited capacity for repair as it does not contain any blood vessels, and so where damage has occurred the growth of new tissue is extremely slow, if at all.

Interference in the hip joint can be eliminated by removing any bone tissue which interferes with movement of the joint. Typically, interference occurs from naturally occurring irregularities, known as Cam lesions or femoral neck bumps, on the otherwise generally spherical head of the femur. These are commonly removed by surgeons during open hip surgery. During the procedure the surgeon will utilise a generally spherical template by placing it over the generally spherical head of the femur, and then sliding the template around the femoral head until any gaps that occur, between the template and the femoral head are observed. These gaps indicate a change in curvature, and any discrepancies or blimps can then be removed by, for example, a chisel or powered burr, to allow the joint to move without impedance.

Whereas, in the current arthroscopic approach, the surgeon must make an educated guess of where the "bump" is. Due to distortion of the arthroscopic image in the joint during the procedure, the awkward direction of view of the arthroscope used in hip and the difficulty of interoperatively moving the femur through its full range of motion, it is a clinical challenge to arthroscopically determine where and how much bone should be removed. Typically, a surgeon will remove some, of the bump and then flex the hip to see if the joint is still impeded. This is difficult and often impractical as the arthroscopic view becomes occluded by soft tissue with this motion.

A more convenient arthroscopic approach could have considerable advantages over open surgical procedures if these obstacles were overcome. In particular, it would lead to a quicker rehabilitation with, less chance for iatrogenic damage when dislocating the joint. Accordingly, there exists a need for a fully integrated arthroscopic approach.

The present invention seeks to overcome the above issues by providing an arthroscopic device which can be used to mark a bone growth or irregularity in the surface of a bone, and any overlying cartilage tissue, so that mechanical devices can be used subsequently to remove it arthroscopically.

In a first aspect of the present invention there is provided a surgical instrument comprising a shaft having a handle towards a proximal end and an arm towards a distal end, wherein the arm comprises a template, and the arm and/or template includes tissue marking means for marking differences in the curvature of a tissue surface.

Preferably, the tissue surface is formed of cartilage or bone.

Suitably, the arm is connected to the distal end of the shaft by a resiliently flexible member. Suitably, the resiliently flexible member is configured to bias the template towards the tissue surface. Suitably, the resiliently flexible member comprises a Nitinol wire, a Nitinol tube, a spring, a live-hinge or a corrugated portion.

Alternatively, the arm is pivotally connected at the distal end of the shaft. Suitably, the arm has proximal and distal ends and is pivotally connected therebetween. Preferably, the pivotal connection allows the arm to pivot within a single plane. Optionally, the pivotal connection is a universal joint or a ball-and-socket joint. Suitably, the universal joint or a ball-and-socket joint includes a lock to restrict motion of the joint to a single plane.

The flexibility in the arm, relative to the shaft, allows the template to accurately follow the contours of the tissue surface and enables changes in the curvature of the tissue surface to be identified.

In further alternative embodiments, the arm is connected with and is substantially rigid relative to the shaft.

Suitably, the template includes a tissue engaging surface. Suitably, the tissue engaging surface is curved. Preferably, at least a portion of the template directly engages with the tissue surface which includes tissue to be marked. Alternatively, the template engages with a tissue surface which is complementary to the tissue surface which includes tissue to be marked. In use, the tissue engaging surface of the template allows a surgeon to observe differences in the curvature of a tissue surface by monitoring any deviations in gaps which appear between the template and the tissue surface as the template is moved across the tissue surface.

Suitably, the marking means is a sharpened tip or blade; suitably, located at an end of the arm. Preferably, the marking means is located towards a proximal end of the arm. Alternatively, the marking means is an aperture or channel in the arm comprising a sharpened edge or blade. In this alternative embodiment, the sharpened edge or blade can be used to mark or selectively resect tissue by sequentially passing the instrument over a particular region to shave the tissue. Alternatively, the marking means comprises an ink or dye; suitably India ink.

Alternatively, the marking means is a radio frequency electrode. Preferably, the radio frequency electrode can be selectively energised to mark a region of the tissue surface. Preferably, the surgical instrument comprises control means for the radio frequency electrode. The control means permit the radio frequency electrode to be selectively energised for a fixed period of time, to minimize collateral damage of surrounding tissue. A particular advantage of radio frequency marking means is that marking of the tissue only occurs when the electrode is activated. This means that these instruments are especially accurate, and also allow the surgeon to identify differences in the curvature of a tissue surface and move the template back and forth over the region of difference, before deciding to mark the region. The tissue surface will only be marked when the surgeon energises the electrode, and at all other times the electrode will not be energised, and so damage to tissue will be highly selective.

In alternative instruments employing a radio frequency electrode, the electrode may be activated by suitable sensing means, or automatically through the application of pressure when it comes into contact with a bump.

Preferably, the instrument further comprises deployment means. Suitably, the deployment means is a solid cylindrical member or a hollow tubular, member. Suitably, the deployment means is a rod or wire attached to the arm; preferably towards the proximal end of the arm. Preferably, the deployment means is a tubular member coaxially mounted with the instrument shaft. Preferably, the deployment means includes an opening at a distal end. Suitably, the deployment means is internally mounted within the instrument shaft.

Preferably, the deployment means is slidably or rotatably mounted within the shaft and interlocks with the template such that it may be held rigidly.

Alternatively, the tubular member is an outer sheath, mounted on the outer surface of the instrument shaft. Preferably, the outer sheath at least partly surrounds a portion of the outer surface of the shaft. Suitably, the outer sheath is slidably mounted or rotatably mounted on the shaft. In embodiments in which the outer sheath is rotatably mounted on the shaft, the rotatable movement arises from a thread and complementary groove arrangement—for example the outer surface of the shaft may include a helical thread.

Preferably, the surgical device includes a lock to prevent the deployment means from impeding movement of the arm when in a deployed position, and for locking the instrument in an arm-stowed position to protect the template in transit. The lock may be any suitable locking means, such as a twist-lock, button or catch.

In use, manipulation of the deployment means moves the arm between a stowed position, in which the arm is aligned substantially with the longitudinal axis of the shaft, and a deployed position, in which the angle between the proximal end of the arm and the shaft is between around 5 degrees and 100 degrees. In particular, distal advancement of outer sheath, relative to the shaft, causes the template arm to align substantially axially with the longitudinal axis of the shaft, and in a stowed position. This is particularly useful for when the instrument is being passed into, and out of, a cannula. Proximal advancement of the outer sheath, relative to the shaft, permits the template arm to pivot relative to the shaft and to deploy.

In alternative embodiments, not shown, the arm will operate in a wider range relative to the shaft. For example, when utilised in other joints or in instances where the surgical instrument is to be introduced into the joint from unforeseen portal trajectories.

In preferred embodiments, the opening of the outer, sheath is axially elongated between a distal end at the distal end of the outer sheath and a proximal end disposed proximally of the arm, thereby to expose, the arm along one side of said outer sheath and define a portion of said outer sheath that provides a hood, for an opposite side of the arm. The outer sheath acts to protect the arm of the instrument when it is in a stowed position and being moved to a surgical site.

Preferably, the outer sheath opening is axially elongated so that the proximal end of the opening is disposed adjacent to the proximal end of the arm.

Suitably, the instrument also includes a biasing means, to bias the arm and template towards the tissue surface. Suitably, the biasing means may be the deployment means. Alternatively, the biasing means is a rod which is biased to extend the arm distally. Suitably, the rod includes a spring or dampener. In use, the biasing means acts to press the distal end of the arm and template against the tissue surface upon which the instrument is being used. This has the effect that the tissue surface is more accurately tracked when the instrument is passed over it, so that differences in the curvature of, for example, the femoral head can be more accurately identified and marked.

Optionally, the template arm further comprises one or more bearings which assist movement of the template arm over a surface. Suitably, the template arm comprises two, three, four, five or six bearings. Preferably, the template arm comprises two bearings. Preferably, the bearings are located towards distal and proximal ends of the template. The provision of one or more bearings allow the arm and template to move more easily over the tissue surface.

Optionally, the instrument further comprises a burr.

In a second aspect of the present invention there is provided a surgical instrument comprising a delivery means and a marking means.

Preferably, the marking means is a paper or film. Preferably, the marking means further includes a pressure-sensitive deployable surface. Suitably, the deployable surface comprises an ink or dye; suitably India ink. Suitably, the marking means is a carbon paper comprising a carrier sheet and a transferable marking substance. Alternatively, the marking means comprises an ink or dye; suitably India ink. An advantage of this system is that the marking process is quick, simple and does not cause any damage to the tissue surface being marked.

Suitably, the delivery means is a grasper.

The above and other aspects of the invention will now be described with reference to the following drawings in which.

Figure 1:
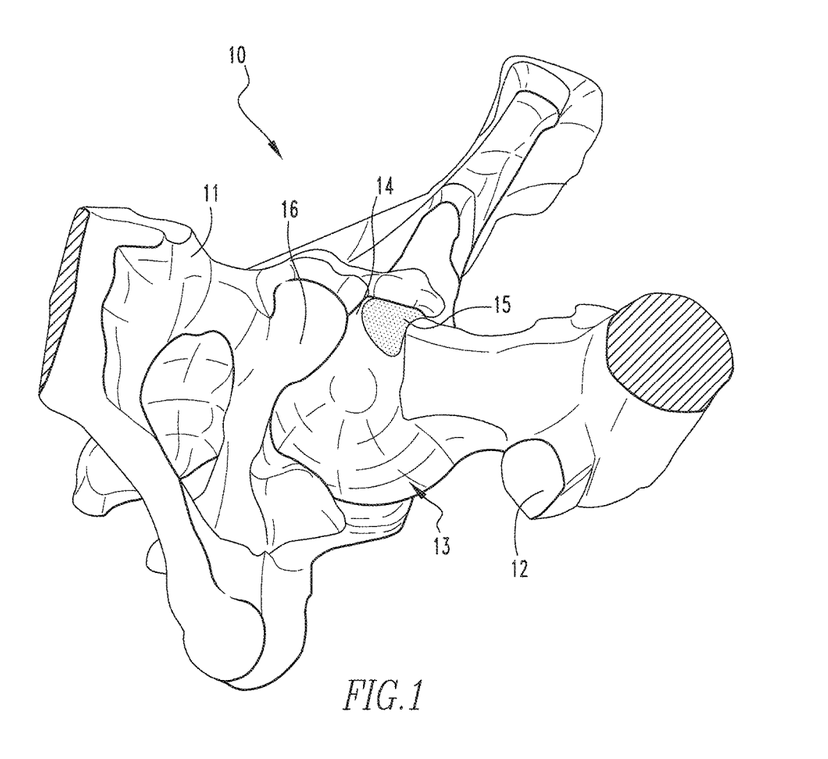
FIG. 1 is a partial view of a hip joint.

Referring to FIG. 1, there is shown a hip, or acetabulofemoral joint 10, formed from the femur 12 and acetabulum of the pelvis 11. Femur 12 includes a substantially spherical head 13, which locates in the cup-like acetabulum of the pelvis 11. The joint is lubricated with synovial fluid and its surfaces are lined with cartilage to cushion movement and allow it to move freely (not shown). The acetabulum, is lined with the acetabular labrum, which is a ring-shaped fibrocartilaginous lip. The labrum extends beyond the acetabulum, forming a tight sliding connection with the femoral head and providing a stable joint.

The purpose of the hip joint is to support the weight of the body in both static and dynamic postures. Huge loads are placed upon the hip joint and any restrictions within the joint, such as bumps, can lead to significant damage to the surfaces of the joint over time.

Figure 2:
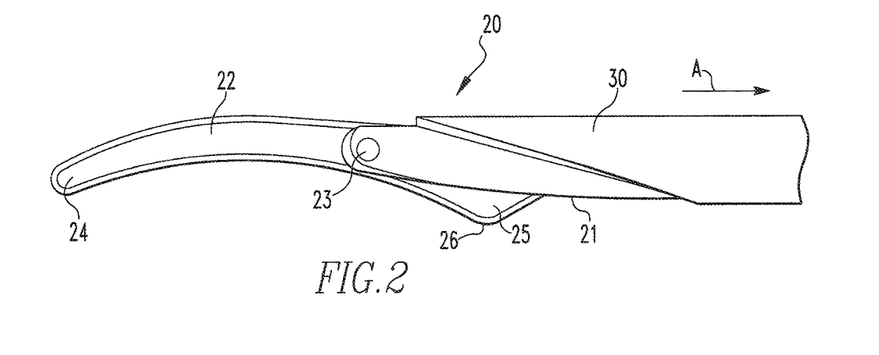
FIG. 2 is an embodiment of an instrument according to the first aspect of the invention, in a retracted position.
Figure 3:
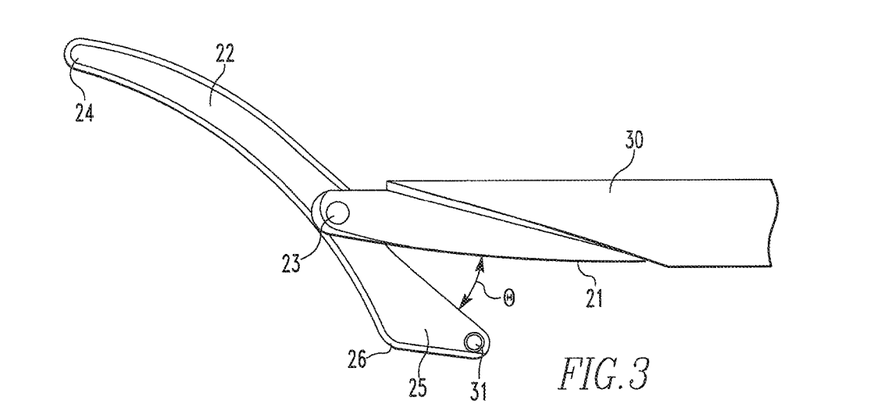
FIG. 3 is the embodiment of FIG. 2 in a deployed position.

In FIGS. 2 and 3 there is shown a partial view of a surgical instrument 20 in accordance with one embodiment of the present invention. The instrument 20 comprises a shaft 21, the distal end of which is shown in FIGS. 2 and 3. The shaft includes an arm 22 pivotally connected through pivot 23. The arm 22 is curved, having a lower concave region and an upper convex region, according to the illustration, with the lower concave region defining a template for a femoral head. The arm is suitably dimensioned to allow it to fit between the femoral head and acetabulum without it being necessary to distract the hip joint. In alternative embodiments, not shown, the arm may be shaped appropriately to provide a template for a different joint such as, for example, the ankle.

Arm 22 includes distal and proximal ends, 24 and 25 respectively, either or both of which may incorporate one or more bearings (not shown). These bearings permit the arm and template to move more easily over the tissue surface, in this particular case the femoral head, in use.

Figure 4:
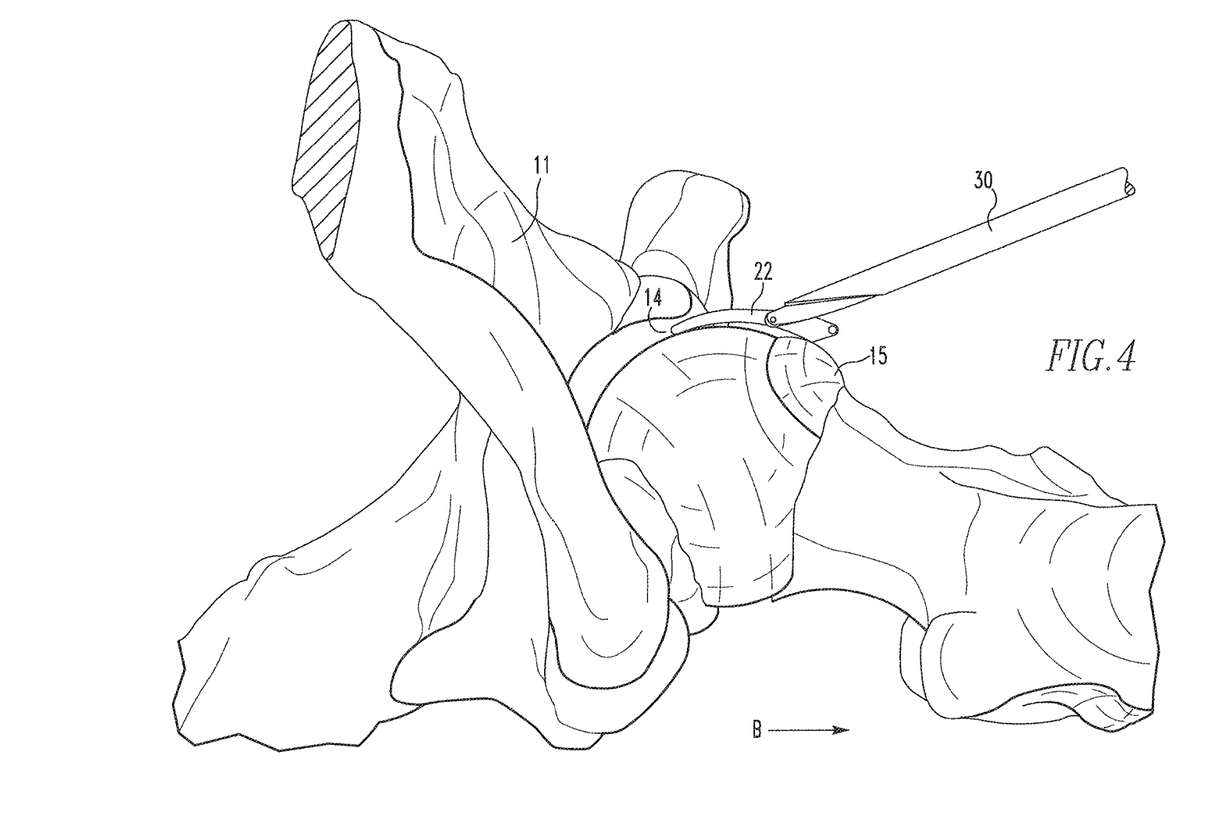
FIG. 4 is the embodiment of FIG. 2 shown in-situ.

The lower concave region of the template has a curved profile that broadly matches the curvature of the femoral head. Such curvature allows the template to be mapped over the tissue surface, and where any gaps appear between the curved lower surface of the template and the tissue surfaces this will help to highlight any changes in the curvature of the femoral head (FIG. 4). The surgical instrument will have a variety of different sizes so that an appropriate instrument can be selected to suit the particular characteristics of a patient's acetabulofemoral joint.

Figure 5:
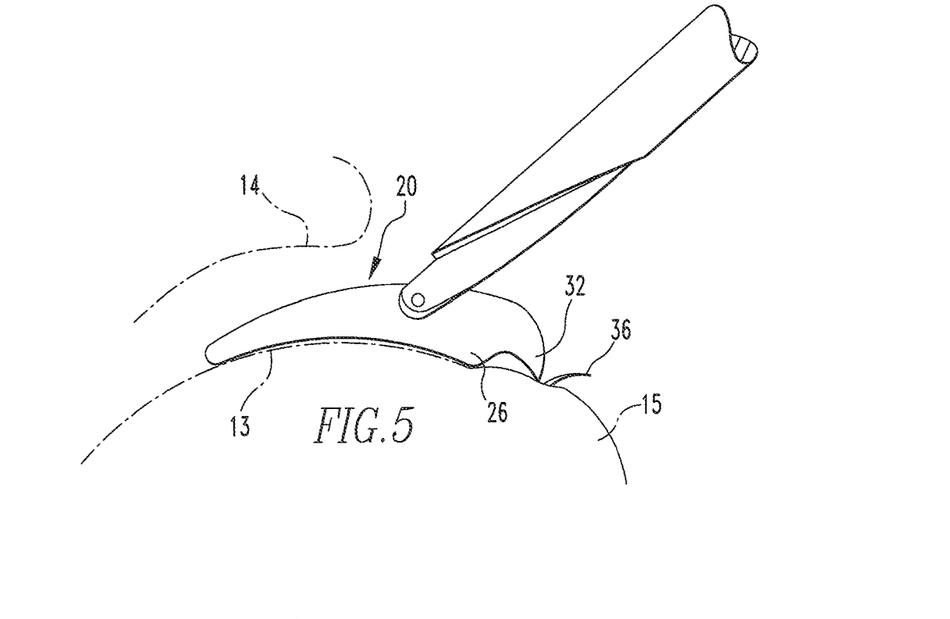
FIG. 5 is a schematic close-up view of an embodiment of FIG. 4 that incorporates a blade.

The template and/or arm 22 also incorporate a marking means in the form of a sharpened tip or blade 32 at, or towards, the proximal end 25 (FIG. 5). The sharpened tip or blade 32 is designed to leave one or more marks 36 on the cartilage covering the femoral head when the template is moved in a generally distal to proximal manner. These marks help to identify changes in the curvature of the femoral head, i.e. where the femoral head "bump" begins. In preferred embodiments, the sharpened tip or blade 32 is located on the heal 26 of the arm, or just proximally thereof, so that marking 36 only occurs with notable changes in the curvature of the femoral head, and not when relatively minor differences are encountered by the template. As can be seen in FIG. 5, as the instrument 20 is moved in a generally distal to proximal direction, blade 32 digs into the cartilage which covers a bump, causing it to nick 36 or shave the cartilage in that region. This disturbance in the tissue surface can be used to positively identify the bump and facilitate its subsequent removal. It is possible, where the bump or irregularity is small or slight, to use the blade to remove it by successive shaving, and provide a smooth transition through the cartilage and into the subchondral bone.

Figure 5A:
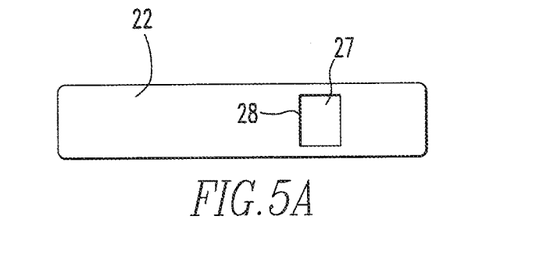
FIGS. 5A-C are schematic illustrations of alternative embodiments of the instrument.
Figure 5B:
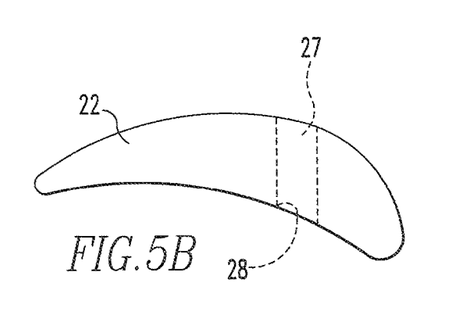

In alternative template arm embodiments, shown in FIG. 5A and in section in FIG. 5B (only arm shown for clarity), the marking means is an aperture or a channel 27 which passes through arm 22. The aperture or channel 27 has a sharpened distal edge 28, so that when the instrument is drawn distal to proximal the sharpened edge marks the bump. Repeated drawing over the region of the bump, can be used to shave and reduce, or remove the bump. Alternatively, the aperture or channel has a sharpened proximal edge. In a further alternative means of marking irregularities in a tissue surface (not shown), an ink or dye suitable for marking a tissue surface is released by, for example, direct injection from a port within the arm or template. The port is suitably located at, or towards, the proximal end of the template or arm. Alternatively, the ink can be delivered from a pen. The pen may be located within, or attached to, the instrument shaft, template or arm. The pen can be retractable. In such embodiments, as the marking means contacts the bump, ink is deposited to thereby mark and identify the irregular shaped region.

Figure 5C:
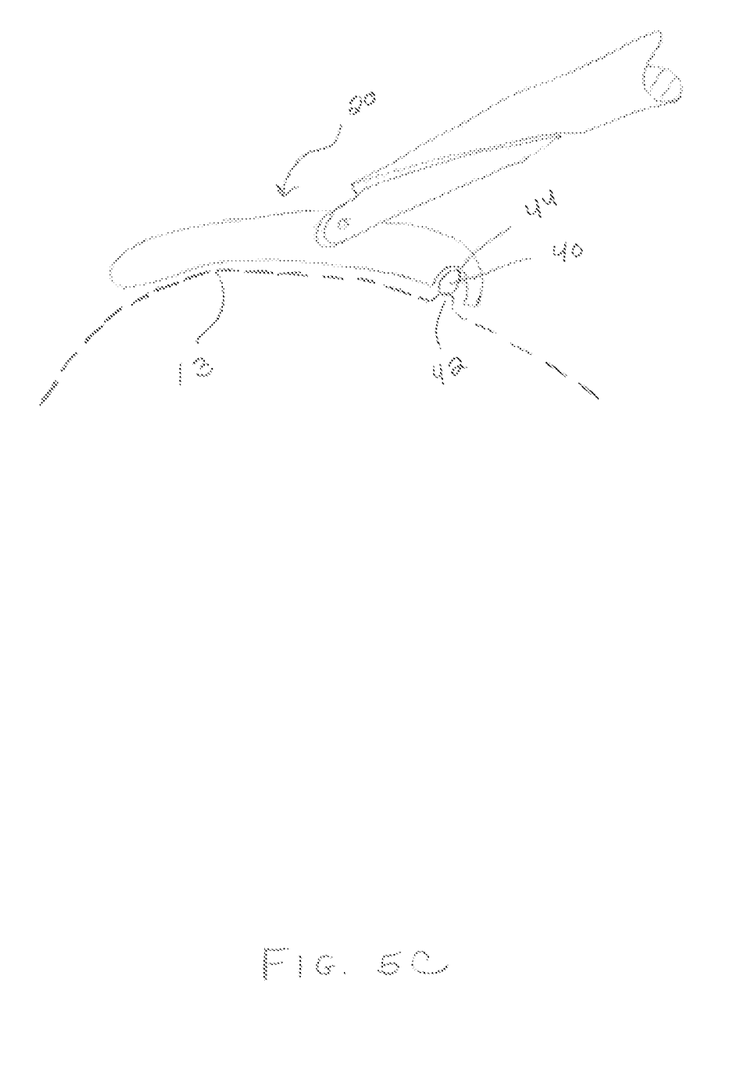

In preferred alternative embodiments, shown in FIG. 5c, the marking means is a radio frequency electrode 40. This RF electrode 40 can be electrically energized when a mark is to be made on the bone or cartilage surface. In such embodiments, the lower concave region of the template may be designed with a recess 44, or so that the concavity is not uniform in order to accommodate the electrode 40. This allows the electrode 40 to be fitted to the template, leaving a small amount of clearance between the template 40 and femoral head 13 when the template is mapped over regions of 'normal' curvature. When such a template encounters a bump 42, the electrode 40 comes into contact with the bump 42 and may be automatically activated to mark it as a result of the contact between the electrode 40 and bump 42. In this manner, the instrument 20 can be used to accurately mark the perimeter of a bump. In alternative embodiments, the electrode 40 may be activated manually by the surgeon who will energize the electrode 40 by pressing a button on the instrument handle or foot pedal (not shown). The advantage of this arrangement is that the surgeon can selectively mark the bump 42, moving the instrument 20 over the site a number of times, and not marking it until they are satisfied that they have correctly identified a bump, so that he or she can be sure of the region being marked.

A further alternative marking means, not as described above, also comprises an ink or dye. This will be discussed in greater detail below in relation to FIGS. 7 and 8.

In further alternative embodiments, not shown, the arm is connected with and is substantially rigid relative to the shaft. In these embodiments, the substantially spherical shape of the template is incorporated in the side edges of the arm, so that the template is utilised with the arm in a side-on orientation. In this case, rotating the shaft of the surgical instrument allows the arm to roll relative to the tissue surface. This is different to the sliding action utilised in the other described embodiments. The marking means is also wrapped around the edges of the arm so that it may engage with and mark tissue regardless of orientation.

In FIGS. 2-4, and 6, shaft 21 is partly surrounded by a retractable outer sheath 30. Outer sheath 30 can be moved in an axial direction, and as is shown in greater detail in FIGS. 2 and 3, in which outer sheath 30 has been retracted in the direction indicated by arrow A, towards a proximal handle (not shown). The outer sheath may be moved by means of an axial thread, slid up and down the shaft, or may include a combination of both—for example, it may be advanced and retracted in a sliding manner and incorporate a twisting or screwing action at or towards the extreme ends of its desired motion in order to lock the sheath in position.

Although FIG. 2 illustrates the arm 22 in a deployed position, with the outer sheath retracted, and may freely move about pivot 23, it is shown in the position in which it is held when the outer sheath 30 is distally advanced and the arm 22 is said to be in a retracted position. This allows the surgical instrument 20 is be easily passed down a cannula and into a surgical site. The outer sheath also acts to house and protect the delicate template, where the sheath has been advanced distally and the arm is in a retracted position. Further, in preferred embodiments, the outer sheath 30 may also act as a deployment means causing the arm and template to move into a stored position.

In a deployed position, the angle θ between the proximal end of the arm and the shaft, and thus the operating range, is between around 5 degrees and 100 degrees.

Figure 9:
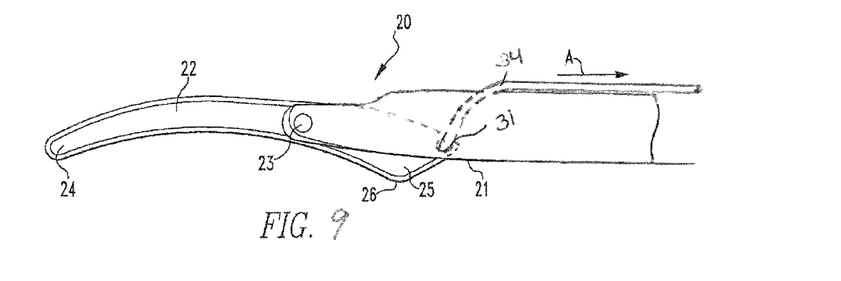
FIG. 9 is an embodiment of the instrument according to another aspect of the invention, in a retracted position.
Figure 10:
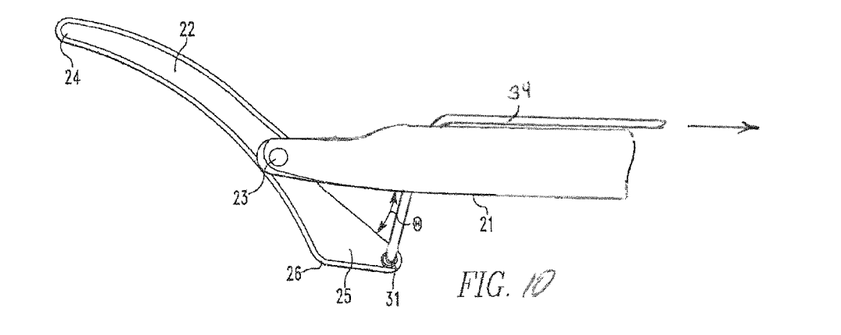
FIG. 10 is the embodiment of FIG. 9 in a deployed position.

In alternative embodiments the deployment means is one or more rods or wires 34, attached proximally to the arm 22 through aperture 31 (FIGS. 9 and 10). The rods or wires 34 are linked to a mechanism, preferably formed with the instrument handle, and are used to deploy the arm 22 and template from a retracted position to a deployed position. For example, a pull wire 34 may be fixed to the proximal end of arm 22 at, or in the region of, aperture 31 thus inducing rotation of the arm 22 about the pivot 23 when the wire 34 is pushed or pulled by the user. In embodiments as described above, the template is only allowed to pivot in a single plane and so only a single rod or wire 34 is necessary to control and manipulate the arm 22. However, in alternative embodiments (not shown) the template and shaft 21 may be articulated in more than one plane. For example, the pivot 23 may be a universal joint or a ball and socket joint. Such arrangements preferably require a pair of rods or wires 34 as deployment means. In embodiments where the pivot 23 is a universal joint or a ball and socket joint, the instrument 20 may also include a lock to restrict motion of the joint to a single plane.

In use, the instrument is passed through a cannula and located in the surgical site of a joint. The arm is then deployed by retracting the outer sheath, or by suitably manipulating the rod or wire. The instrument can then be used to mark any differences in the curvature of a tissue surface which are deemed to impede movement of the joint. After the tissue has been marked, the outer sheath is advanced distally thereby forcing the arm into a stowed position. The instrument can then be withdrawn, and appropriate surgical instruments used subsequently to remove the marked tissue.

Figure 6:
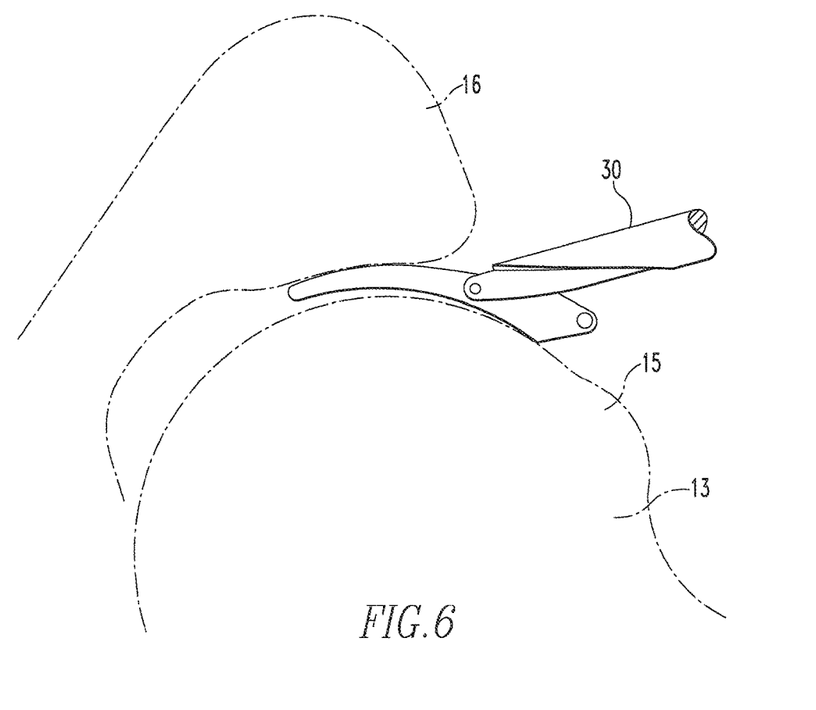
FIG. 6 is an alternative use of the embodiment of FIG. 2.

An alternative way use of the surgical instrument is illustrated in FIG. 6. As shown, the upper and lower surfaces of the instrument template are utilised to respectively engage with the corresponding acetabular and femoral head surfaces. In this arrangement the concave surface of the acetabular socket is used to guide the template, rather than the convex femoral head. In an analogous manner to the marking process using the template described above, marking is carried out by moving the distally to proximally. Accordingly, the distal upper surface of the template engages with the concave inner surface of the acetabulum, and the proximal lower surface of the template engages with the femoral head. As the template is moved in the distal to proximal direction, the template moves over the respective surfaces of the acetabulum and femoral head. However, when the portion of the template which is engaged with the femoral head encounters a difference in the curvature, in the form of a bump, it digs in to the bump and thereby marks it.

In alternative embodiments, not shown, the instrument also includes a biasing means to bias the arm and template towards the tissue surface. The biasing means may be the deployment means, or a separate rod which is biased to extend the arm distally. The rod may include a spring or dampener. In use, the biasing means acts to press the distal end of the arm and template against the tissue surface upon which the instrument is being used. This increases the accuracy of the instrument to enable differences in the curvature of a joint surface to be more accurately identified and marked.

As not all joints are spherical, these concepts may be used to extend to substantially non-spherical joints, such as the ankle joint which is more cylindrical than spherical.

Figure 7:
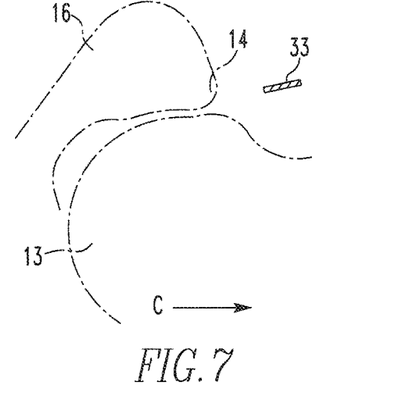
FIG. 7 is schematic illustration of a method of marking in accordance with the second aspect of the invention, prior to the introduction of marking means into the joint.
Figure 8:
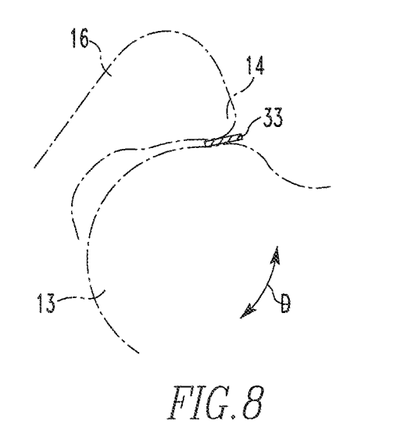
FIG. 8 is schematic illustration of a method of marking in accordance with the second aspect of the invention, with marking means located in the joint.

The clinical technique of all embodiments concerning the first aspect of the invention does not require for the joint to be fully distracted due to the arm of the instrument being suitably dimensioned to slip unimpeded between the femoral head without distraction, where the joint being investigated and treated is the hip. However, it may be desirable to partly distract the joint enough to allow the arm of the surgical instrument to have greater access to the joint. Referring now to FIGS. 7 and 8, there is shown a further alternative means of marking irregularities in a tissue surface. According to this method, a paper or film 33 is introduced into the space of a distracted hip joint, between the acetabulum 16 and the femoral head 13, in the region of the rim of the acetabulum 14. The joint is then allowed to return to its weight bearing, non-distracted, state leaving the paper or film 33 trapped between the femoral head 13 and the rim of the acetabulum 14. The paper or film 33 comprises at least one surface which comprises an ink or dye suitable for marking a tissue surface. This at least one surface is laid facing the surface of the femoral head so that, when the femur is rotated (represented by D), ink or dye will deposit on any surfaces where the movement of the joint is impeded, for example by irregularities in the curvature of the femoral head, such as a bump. In alternative embodiments, not shown, the paper or film 33 has two surfaces, each of which comprises a suitable ink or dye.

Once the appropriate surfaces have been, marked, the paper or film 33 can be removed from the surgical site, and then the bump removed subsequently.

The described arthroscopic approaches could provide considerable advantages over traditional, open surgery, methods. In particular, these instruments and techniques could lead to a quicker rehabilitation with less chance for iatrogenic damage when dislocating the joint.

Although specifically described in the context of the femoral head, it will be recognised that the instrument could be used in other suitable joints such as the ankle.

The invention claimed is:

1. A surgical marking instrument comprising:
   a shaft having a proximal end, a distal end, and a longitudinal axis extending therebetween, a handle being coupled to the proximal end of the shaft;
   an arm pivotally connected towards a distal end of the shaft, the arm having first and second opposing surfaces and dimensioned to fit between a head and socket of a joint, the second surface of the arm comprising a curved template, a curvature of the template configured to engage a complementary surface of a normal curvature of the joint head, the template further defining a recess located towards a proximal end of the arm;
   a rod or wire attached to the proximal end of the arm for inducing rotation of the arm about the pivotal connection; and
   a radio frequency electrode fitted to the recess;
   wherein the arm is connected to the shaft closer to a midpoint between the proximal end and a distal end of the arm to allow the template to change orientation relative to the longitudinal axis of the shaft;
   wherein the template is further configured to allow a user to observe a difference in the normal curvature of the joint head defined by gaps between the template and an abnormal curvature of the joint head as the template is moved over the surface; and
   wherein, when the template encounters the difference in the normal curvature, the electrode is configured to mark a perimeter of the difference.

2. An instrument as claimed in claim 1, wherein the pivotal connection allows the arm to pivot within a single plane between an angle of 5 degrees and an angle of 100 degrees, the angle formed between the proximal end of the arm and the shaft.

3. An instrument as claimed in claim 1, wherein the pivotal connection comprises a universal joint or a ball-and-socket joint.

4. An instrument as claimed in claim 1, wherein the arm is connected to the distal end of the shaft by a resiliently flexible member.

5. An instrument as claimed in claim 4, wherein the resiliently flexible member is configured to bias the arm towards the tissue surface.

6. An instrument as claimed in claim 5, wherein the resiliently flexible member comprises a Nitinol wire, a Nitinol tube, a spring, a live-hinge or a corrugated portion.

7. An instrument as claimed in claim 1, wherein the rod or wire interlocks with the template such that the template may be held rigidly relative to the shaft.

8. An instrument as claimed in claim 1, wherein the first surface of the arm is engageable with the joint socket concurrently with engagement of the second surface of the arm with the joint head.

9. An instrument as claimed in claim 1, wherein the surgical instrument further comprises a controller in electrical communication with the radio frequency electrode, the controller adapted to selectively energize the radio frequency electrode for a fixed period of time.

10. An instrument as claimed in claim 9, wherein the controller comprises a button mounted on the handle or a foot pedal for energizing the radiofrequency electrode.

11. An instrument as claimed in claim 1, wherein the rod or wire is internally mounted within the shaft.

12. An instrument as claimed in claim 1, wherein the instrument also comprises a biasing mechanism adapted to bias the arm towards the joint head.

13. An instrument as claimed in claim 12, wherein the biasing mechanism is the instrument shaft, or a separate rod, spring, live-hinge or dampener which is biased to extend the arm distally.

14. An instrument as claimed in claim 13, wherein the rod includes a spring or dampener.

15. An instrument as claimed in claim 1, wherein the arm further comprises one or more bearings which assist movement of the template over the surface.

16. An instrument as claimed in claim 15, wherein the arm comprises two, three, four, five or six bearings.

17. An instrument as claimed in claim 1, wherein the arm is dimensioned to slip unimpeded between the joint head and socket without distraction of the joint.

18. An instrument as claimed in claim 1, wherein the electrode is different than the arm.

19. An instrument as claimed in claim 1, wherein the template further comprises a first region of uniform curvature and a second region of non-uniform curvature, wherein the radiofrequency electrode is fitted into the second region of the template.

20. A surgical marking instrument comprising:
a shaft having a proximal end, a distal end, and a longitudinal axis extending therebetween, a handle being coupled to the proximal end of the shaft;
an arm pivotally connected towards a distal end of the shaft, the arm having first and second opposing surfaces and dimensioned to fit between a head and socket of a joint, the second surface of the arm comprising a curved template, a curvature of the template configured to engage a complementary surface of a normal curvature of the joint head, the template further defining a recess located towards the proximal end of the arm;
a radio frequency electrode fitted to the recess;
a hollow tubular member dimensioned to receive the shaft and adapted to move axially along the shaft, an opening of the tubular member being axially elongated between a distal end at a distal end of the tubular member and a proximal end disposed proximally of the arm;
wherein the arm is connected to the shaft closer to a midpoint between proximal and distal ends of the arm to allow the template to change orientation relative to the longitudinal axis of the shaft;
wherein the template is further configured to allow a user to observe a difference in the normal curvature of the joint head defined by gaps between the template and an abnormal curvature of the joint head as the template is moved over the surface; and
wherein, when the template encounters the difference in the normal curvature, the electrode is configured to mark a perimeter of the difference.

21. An instrument as claimed in claim 20, wherein the tubular member is coaxially mounted to the shaft and wherein proximal movement of the tubular member places the arm in a deployed position, where the arm is free to move about the pivotal connection, and distal movement of the tubular member forces the arm into a retracted position where at least a portion of the arm is housed within the tubular member.

22. An instrument as claimed in claim 20, wherein the hollow tubular member is slidably or rotatably mounted on the instrument shaft.

23. An instrument as claimed in claim 20, further comprising a lock that inhibits axial motion of the hollow tubular member.

* * * * *